US006656223B2

(12) United States Patent
Brady

(10) Patent No.: US 6,656,223 B2
(45) Date of Patent: Dec. 2, 2003

(54) FOLDABLE INTRAOCULAR LENSES WITH HIGHLY FLEXIBLE OPTICS AND RIGID FIXATION MEMBERS

(75) Inventor: Daniel G. Brady, San Juan Capistrano, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 13 days.

(21) Appl. No.: 09/943,549

(22) Filed: Aug. 30, 2001

(65) Prior Publication Data

US 2003/0045933 A1 Mar. 6, 2003

(51) Int. Cl.[7] .................................................. A61F 2/16
(52) U.S. Cl. ..................... 623/6.46; 623/6.43; 623/6.54
(58) Field of Search ........................... 623/6.11, 6.18, 623/6.38–6.39, 6.4, 6.41–6.43, 6.45–6.47, 6.54, 6.56

(56) References Cited

U.S. PATENT DOCUMENTS

| 4,377,329 A | 3/1983 | Poler |
| 4,402,579 A | 9/1983 | Poler |
| 4,435,050 A | 3/1984 | Poler |
| 4,439,873 A | 4/1984 | Poler |
| 4,450,593 A | 5/1984 | Poler |
| 4,466,858 A | 8/1984 | Poler |
| 4,473,434 A | 9/1984 | Poler |
| 4,521,273 A | 6/1985 | Poler |
| 4,571,040 A | 2/1986 | Poler |
| 4,642,116 A | 2/1987 | Clayman et al. |
| 4,687,484 A * | 8/1987 | Kaplan ....................... 623/6.46 |
| 4,711,638 A * | 12/1987 | Lindstrom .................. 623/6.54 |
| 5,141,507 A * | 8/1992 | Parekh ....................... 623/6.46 |
| 5,792,822 A | 8/1998 | Miyabayashi et al. |
| 6,083,261 A * | 7/2000 | Callahan et al. ........... 623/6.38 |
| 6,224,628 B1 * | 5/2001 | Callahan et al. ............. 623/6.4 |
| 2002/0026241 A1 * | 2/2002 | Baikoff ...................... 623/6.46 |
| 2002/0120331 A1 * | 8/2002 | Galin et al. ................ 623/6.49 |
| 2002/0173846 A1 * | 11/2002 | Blake et al. ............... 623/6.18 |

\* cited by examiner

Primary Examiner—David J. Isabella
Assistant Examiner—Urmi Chattopadhyay
(74) Attorney, Agent, or Firm—Stout, Uxa, Buyan & Mullins LLP; Frank J. Uxa; Peter Jon Gluck

(57) ABSTRACT

A foldable intraocular lens for implantation in the eye includes an optic made of a highly pliable material and a pair of fixation members made of a material that is flexible, but more rigid than the optic. The fixation members are integral with a cantilevered arm that extends radially outward from the optic. Each fixation member includes a proximal end at the outer end of the cantilevered arm, a distal end, and a flex portion intermediate the proximal and distal ends. The flex portions of the two fixation member extend generally away from one other adjacent their respective proximal ends on diametrically-opposed sides of the optic.

27 Claims, 3 Drawing Sheets

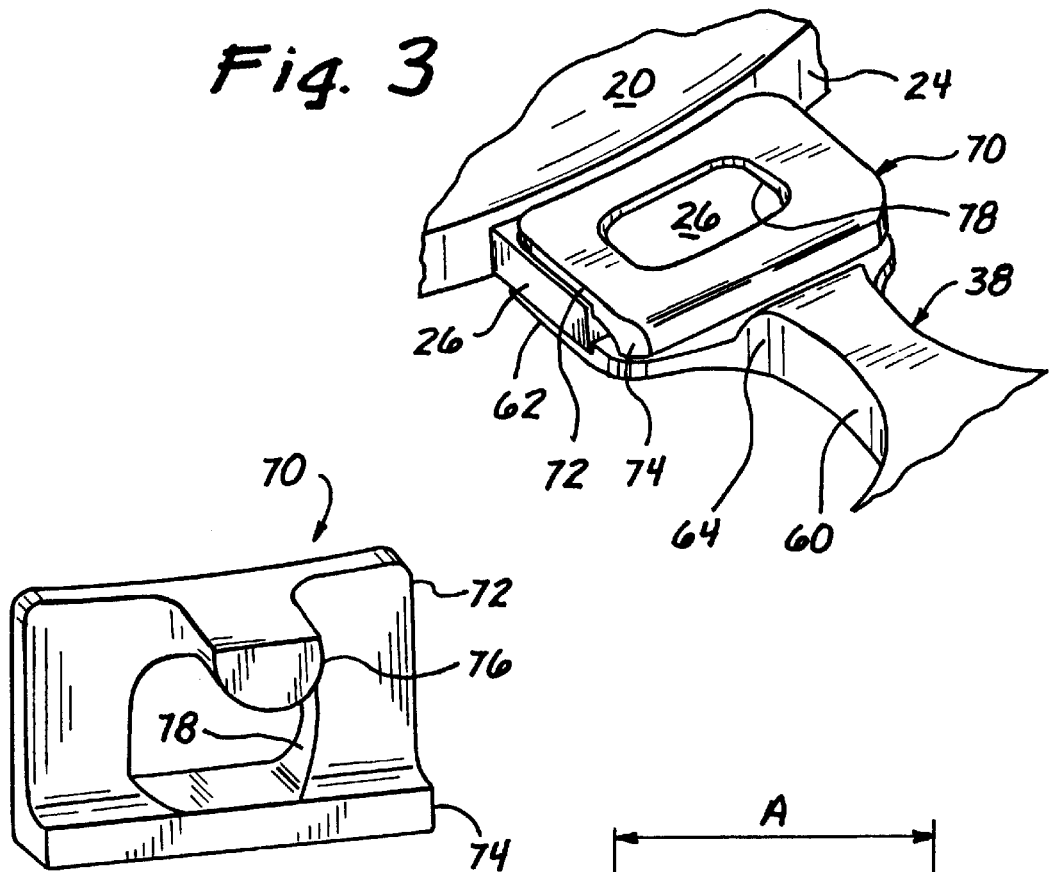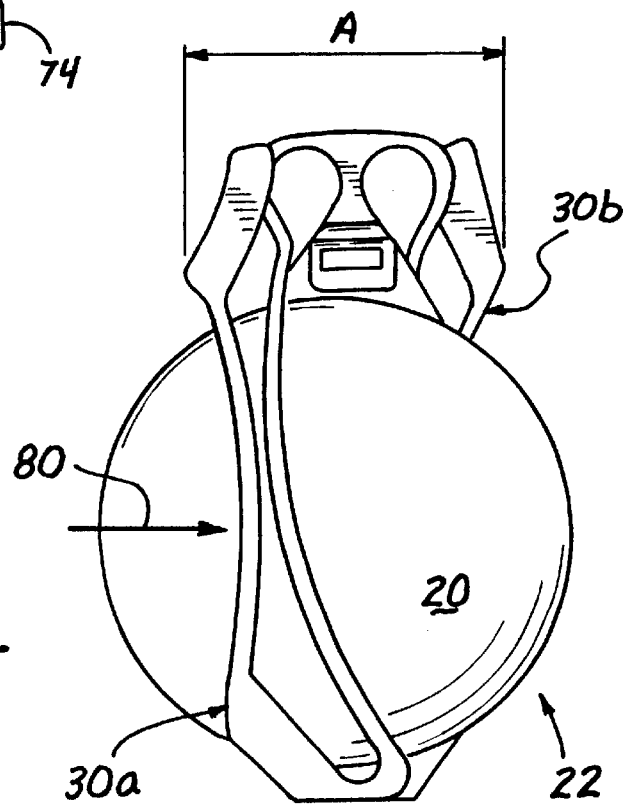

FOLDABLE INTRAOCULAR LENSES WITH HIGHLY FLEXIBLE OPTICS AND RIGID FIXATION MEMBERS

BACKGROUND OF THE INVENTION

This invention relates to intraocular lenses (IOLs). More particularly, the invention relates to foldable IOLs having highly pliable optics and relatively less flexible haptics that may be placed in either the anterior or posterior chamber of the eye through very small incisions.

Intraocular lenses (IOLs) are commonly used to modify or enhance vision. IOLs can be placed at various positions or locations within the eye. For example, IOLs can be placed in the anterior chamber (AC) of the eye, that is, the region of the eye posterior of the cornea and anterior of the iris. Alternatively, a posterior chamber (PC) IOL is implanted behind the iris, typically in the capsular bag from which the natural lens has been removed.

IOLs advantageously have been foldable for insertion through small incisions (less than about 6 mm), particularly for insertion in the capsular bags in the posterior chamber of the eye. IOLs may generally be classed by material. Hard or rigid IOLs are distinguished from soft IOLs that may be folded to facilitate implantation through a small incision in the cornea (and capsular bag for posterior lenses).

A typical IOL has a disk-shaped optic with 2 to 4 fixation members extending outward therefrom. For purpose of orientation, 3:00, 6:00, 9:00, and 12:00 positions around the optic may be defined, thus locating perpendicular 3/9 o'clock and 6/12 o'clock axes. As a matter of convention, a three-piece IOL (i.e., an optic and 2 haptics) is oriented along the 6/12 o'clock axis such that the haptics project outward generally along that axis (so that the haptics are often opposite mirror images of one another across the 3/9 o'clock axis). Four- or five-piece IOLs are oriented likewise. Such IOLs are normally introduced through the incision using a Bartell-style injector, for example as described in Bartell U.S. Pat. No. 4,681,102, the disclosure of which is hereby incorporated herein in its entirety by reference.

A Bartell-style injector folds the optic along the 6/12 o'clock axis, thus defining leading and trailing haptics. The profile of the haptics along the 3/9 o'clock axis is less than about 6 mm so as to fit through small incisions. This means that either a single haptic has a length dimension of less than about 6 mm or that the outermost portions of two haptics are spaced apart less than about 6 mm. Unfortunately, this size limitation reduces the implanted stability of the IOL, increases forces transmitted to the optic which may increase optic displacement, hinders symmetric placement of the IOL within the capsular bag in PC implants, and potentially increase the severity and occurrence of pupil ovalization in anterior chamber implants.

IOLs may be oversized relative to the peripheral anatomical structure and flexible in the plane of the IOL such that they are placed in compression when implanted. Both soft and rigid IOLs exert retention forces on their outer ends that are desirable so that the lens is held in place or centered, otherwise a loose fit might cause vision and other problems. However, a balance must be observed between sufficient compression for a good fit and excessive compression that adversely affects the IOL performance. For example, problems of corneal touch and further endothelial cell loss may arise in some current anterior chamber IOLs, whether formed of soft or rigid materials, which may deflect along the optical axis even with only a small magnitude of compressive fit.

A common technique for placement of an intraocular lens in the anterior chamber is within the iridio-corneal angle, in a so-called "angle-supported" configuration. A number of non-foldable angle-supported anterior chamber intraocular lenses are fabricated from rigid materials, such as polymethyl methacrylate (PMMA). These rigid anterior chamber intraocular lenses are typically based upon a Kelman design of thin, flexible haptics or fixation members with 3 or 4 footplates or pods. Unfortunately, some designs provide less than desirable foldability, or else have minimal compressive retention forces that permits unwanted intraocular lens movement.

It would be advantageous to provide foldable IOLs which provide one or more of the following: reduced incidences of one or more known complications caused by prior anterior chamber IOLs, effective and safe folding for insertion in the eye, safe and effective fit to a range of sizes of eyes, a minimum of translational movement of the optic of the IOL along the optical axis from the compressive fit in the eye, and an otherwise stable optic to avoid unwanted movement.

SUMMARY OF THE INVENTION

New IOLs for implantation in eyes have been discovered. The present IOLs are sized and structured to reduce the incidence of one or more known complications in the eye caused by prior IOLs.

The present invention provides a foldable intraocular lens for implantation in the eye, comprising an optic centered on an optical axis and made of a highly pliable material, the optic having a generally circular periphery and an integral flange extending radially outward therefrom. A cantilevered arm extends radially outward from the periphery of the optic and is made of a material that is flexible but more rigid than the material of the optic, the arm being attached to the optic. A pair of fixation members integral with the cantilevered arm support the optic centered on the optical axis of the eye. Each fixation member has a proximal end at the outer end of the cantilevered arm, a distal end, and a flex portion intermediate the proximal and distal ends. The flex portions extend generally away from one another adjacent to their respective proximal ends on diametrically-opposed sides of the optic.

Desirably, the material of the optic is selected from the group consisting of, silicone, hydrophilic acrylic, and hydrophobic acrylic. The material of the cantilevered arm and fixation members may be selected from the group consisting of PMMA, and polyether sulfone. If the optic is a meniscus type of optic it desirably has a center thickness of less than about 0.5 mm. The fixation members preferably have a thickness and flexibility that enables them to be folded inward toward one another so as to overlap the optic and present a smaller insertion profile than the diameter of the optic.

The cantilevered arm may include a main elongate portion and a paddle that overlaps one side of the flange, and the intraocular lens further includes a coupling member separate from the optic and cantilevered arm. The coupling member preferably includes a portion that overlaps the flange on the side opposite the paddle, and a stepped edge that has approximately the same thickness as the flange. The coupling member and paddle sandwich the flange therebetween and the stepped edge of the coupling member directly contacts the cantilevered arm, wherein the cantilevered arm, flange, and coupling member define an attachment assembly that is bonded together. The attachment assembly is preferably bonded together using a method selected from the group consisting of heat staking, laser welding, and ultrasonic welding.

The flex portions of each fixation member may extend generally away from one another adjacent to their respective proximal ends and then turn about 90 degrees to form substantial U-shapes that have lengths greater than the diameter of the optic, the U-shapes being oriented generally in parallel on diametrically-opposed sides of the optic. When the lens is adapted for anterior chamber implantation, each flex portion of each fixation member includes a pair of spaced apart pods for contacting the iridio-corneal angle in the anterior chamber. Each pair of pods is desirably spaced apart at least seven mm. When the lens is adapted for anterior chamber implantation, each flex portion of each fixation member includes a pair of spaced apart pods for contacting the iridio-corneal angle in the anterior chamber. The four pods are desirably arranged on the flex portions so that upon inward compression of between about 0.5–1.5 mm, they form a square in the iridio-corneal angle so as to reduce the chance of pupil ovalization.

A further aspect of the present invention is a foldable intraocular lens for implantation in the eye, comprising an optic centered on an optical axis and made of a highly pliable material, the optic having a generally circular periphery. A cantilevered arm extends radially outward from the optic periphery and is made of a material that is flexible but more rigid than the material of the optic. The arm is attached to the optic periphery using a method selected from the group consisting of heat staking, laser welding, and ultrasonic welding. A pair of fixation members integral with the cantilevered arm support the optic centered on the optical axis of the eye. Each fixation member has a proximal end at the outer end of the cantilevered arm, a distal end, and a flex portion intermediate the proximal and distal ends, the flex portions being oriented generally in parallel on diametrically-opposed sides of the optic. Desirably, the fixation members have a thickness and flexibility that enables them to be folded inward toward one another so as to overlap the optic and present a smaller insertion profile than the diameter of the optic.

In a still further aspect, a foldable intraocular lens for implantation in the eye is provided. The intraocular lens includes an optic centered on an optical axis and made of a highly pliable material, the optic having a generally circular periphery and an integral flange extending radially outward therefrom. A fixation member supports the optic centered on the optical axis of the eye, the fixation member having a proximal end, a distal end, and a flex portion intermediate the proximal and distal ends, the proximal end having an arm extending toward the optic and a paddle on the end thereof that overlaps the flange and is connected thereto. A coupling member separate from the optic and fixation member includes a portion that overlaps the flange, and a stepped edge that has approximately the same thickness as the flange. The coupling member and paddle sandwich the flange therebetween and the stepped edge of the coupling member directly contacts the arm, wherein the arm, flange, and coupling member define an attachment assembly, the assembly being bonded together.

The fixation member, arm and paddle may being integrally formed of a material that is flexible but more rigid than the material of the optic. Desirably, the material of the arm and fixation members is selected from the group consisting of PMMA and polyether sulfone. The attachment assembly is preferably bonded together using a method selected from the group consisting of, heat staking, laser welding, and ultrasonic welding. The flange may include an aperture and the coupling member has a projection that fits through the aperture and contacts the paddle on the other side of the flange. Preferably, the fixation member arm and paddle and coupling member are made of the same material, in the attachment assembly is bonded together using heat such that the portions in direct contact fuse together.

In accordance with the present invention, a method of folding and inserting an intraocular lens in an eye comprises:
  providing an intraocular lens having:
    an optic centered on an optical axis and made of a highly pliable material, the optic having a generally circular periphery;
    a cantilevered arm extending radially outward from the optic periphery made of a material that is flexible but more rigid than the material of the optic, the arm being bonded to the optic periphery; and
    a pair of fixation members integral with the cantilevered arm for supporting the optic centered on the optical axis of the eye, each fixation member having a proximal end at the outer end of the cantilevered arm, a distal end, and a flex portion intermediate the proximal and distal ends, the flex portions being oriented generally in parallel on diametrically-opposed sides of the optic;
  flexing both of the fixation members toward one another so that they overlap within the diameter of the optic and define an insertion profile of less than about 5 mm; and
  passing the intraocular lens with the fixation members overlapping one another through an incision in the cornea of 5 mm or less without otherwise manipulating the optic into a fold.

The flex portions are desirably oriented generally in parallel on diametrically-opposed sides of the optic, and the flex portions of each fixation member extend generally away from one another adjacent to their respective proximal ends and then turn about 90 degrees to form substantial U-shapes that have lengths greater than the diameter of the optic, the U-shapes being oriented generally in parallel on diametrically-opposed sides of the optic and having inner arms and outer arms. The method of the present invention thus includes flexing both of the fixation members toward one another so that the outer arms overlap the diameter of the optic.

These and other aspects and advantages of the present invention will become apparent in the following detailed description and claims, particularly when considered in conjunction with the accompanying drawings in which like parts bear like reference numerals.

BRIEF DESCRIPTION OF THE DRAWINGS

FIG. 3 is a perspective view of a portion of the intraocular lens of the present invention showing an area of attachment between the optic and a cantilevered arm extending outward therefrom;

FIG. 4 is a perspective view of the underside of a coupling member used to attach the optic to the cantilevered arm; and FIG. 5 is a plan view of the intraocular lens of present invention shown folded in a manner that facilitates implantation through a relatively small incision in the eye.

DESCRIPTION OF THE PREFERRED EMBODIMENTS

The present invention provides intraocular lenses having flexible optic portions enabling folding, and relatively more rigid fixation members or haptics for sufficient and symmetric fixation force.

The present invention provides an intraocular lens that is suitable for implantation in either the anterior or posterior chambers of the eye. In general, lenses of the present invention include ultrathin and highly pliable optics and relatively more rigid haptics, and are suitable for introduction through extremely small incisions in the cornea and in the capsular bag. Lenses of the present invention may be implanted in the eye using conventional injectors (i.e., Bartell-style injectors), or using forceps, or other similar expedient. Various materials may be used in the construction of the lenses described herein, and any particularly preferred construction should not be considered necessarily limiting.

Figure 1:
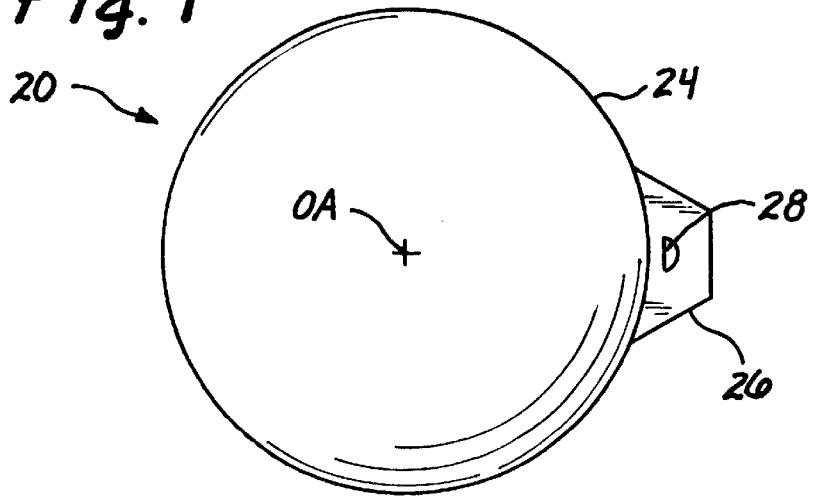
FIG. 1 is a plan view of an optic of the intraocular lens of the present invention.
Figure 2:
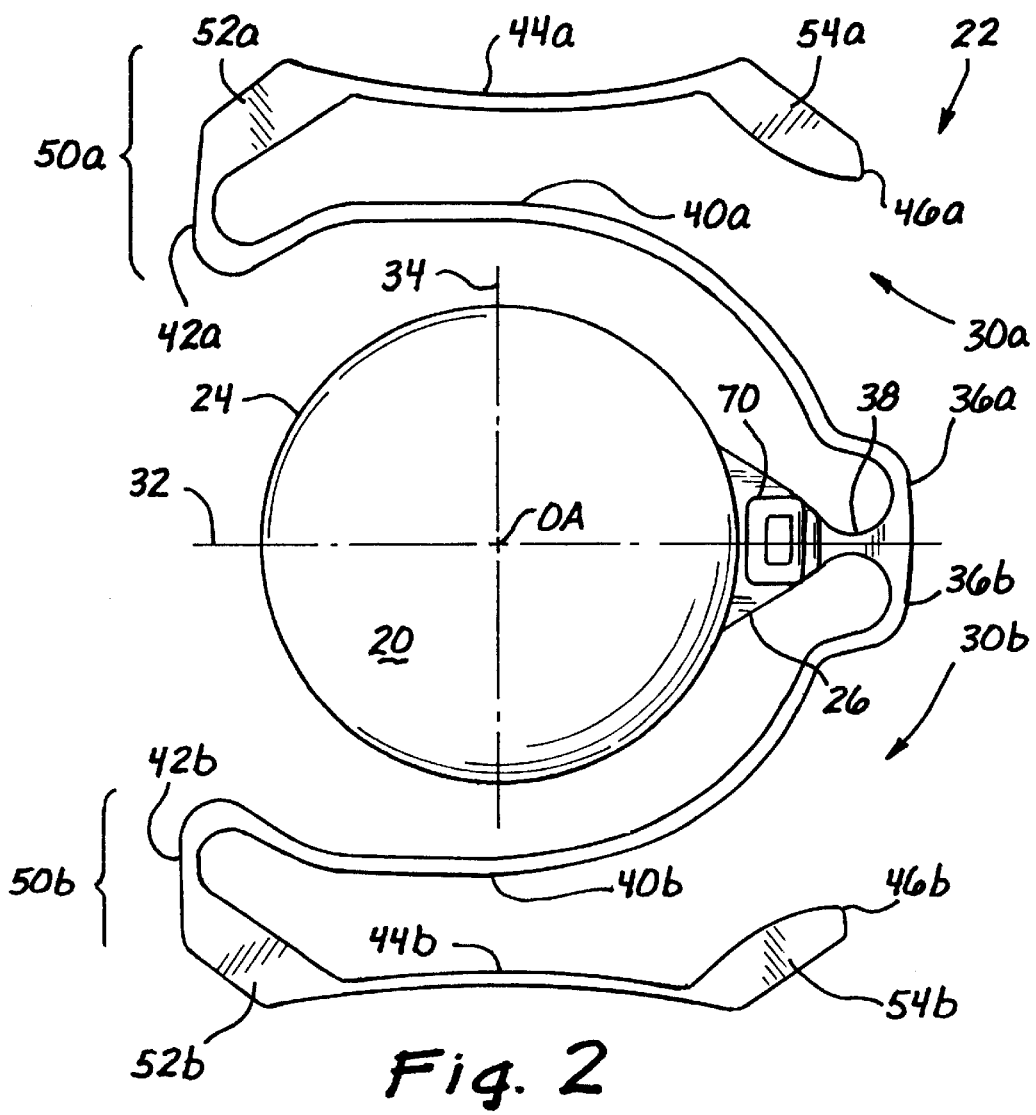
FIG. 2 is a plan view of an exemplary intraocular lens of the present invention.

FIG. 1 illustrates an optic 20 used in an intraocular lens 22 of the present invention as seen in FIG. 2. The optic 20 is generally disk-shaped having a circular periphery 24 centered about an optical axis OA. In addition, a small flange 26 projects outwardly from the periphery 24, and is desirably integrally formed therewith such as by molding from a homogeneous material. The flange 26 may take a variety of forms, and is shown having a generally trapezoidal shape in plan view extending from the three o'clock position on the optic 20. An alternative flange configuration is seen in FIG. 3. The flange 26 desirably includes an aperture 28 therein, to assist in bonding fixation members (described below) to the optic 20.

The optic 20 may be bi-convex, concave-convex (meniscus type), plano-convex, or concave-concave, and have optical powers of between −15 to +30. Again, the optic 20 may be made of a variety of materials, although highly pliable materials such as silicone, hydrophilic acrylic, or hydrophobic acrylic are preferred. Lenses of the present invention have optics that fold and fit through relatively small incisions (less than 5 mm in length). Advantageously, the optics are so thin that they need not be pre-folded before advancing through the incision, but rather inherently fold as they are pushed through the incision, without harming the corneal or capsular bag tissue. Importantly, such thin lenses have not previously been made with the optic separate from the fixation members, but have instead been molded or machined from a single piece.

Quantification of the thickness dimension of the lenses depends on the shape, be it bi-convex, concave-convex (meniscus type), etc, and the diopter power, among other factors. For the concave-convex (meniscus type) of lenses, which are typically favored in the anterior chamber, having negative Diopter values, the optic 20 has a minimum center thickness in the axial direction of between 0.0762 mm to 0.127 mm (0.003–0.005 inches). Therefore, for meniscus type optics, the center thickness may be as small as about 0.13 mm, desirably around 0.1 mm. The edge thickness of such ultra thin meniscus type optics is about 0.4 mm. Meniscus type optics of the present invention have a maximum center thickness (for optics having Diopter powers of 5 or 6) of less than about 0.5 mm. Bi-convex optics of the present invention, in contrast, have a center thickness of around 1.0 mm, and an edge thickness of less than about 0.1 mm.

The intraocular lens 22 seen in FIG. 2 in its relaxed, uncompressed state, includes the aforementioned optic 20 and a pair of fixation members 30a, 30b adapted to support the optic in the center of the eye (whether placed in the anterior chamber, or in the capsular bag in the posterior chamber). For purpose of orientation, perpendicular axes 32, 34 along the horizontal and vertical planes, respectively, are shown. Stated another way, the horizontal axis 32 extends along the 3/9 o'clock plane, while the vertical axis 34 extends along the 6/12 o'clock plane.

Desirably, the fixation members 30a, 30b are formed in a single piece connected at their proximal ends 36a, 36b to the flange 26 via a cantilevered arm 38. In an exemplary embodiment, the fixation members 30a, 30b and cantilevered arm 38 are integrally formed such as by molding from a homogeneous material that is more rigid than that of the optic 20, although still somewhat flexible to enable folding during implantation (described below). Preferred materials are poly methyl methacrylate (PMMA) or polyether sulfone, although other similar materials may be used.

The flange 26 extends along the three o'clock direction, and thus both of the fixation members 30a, 30b initially extend generally vertically in opposite directions from the outermost end of the cantilevered arm 38. From their proximal ends 36a, 36b, the fixation members 30a, 30b each define an elongated, curvilinear inside leg 40, a U-bend 42, and an outside leg 44 that terminates at a distal end 46. The combination of the inside leg 40, U-bend 42, and outside leg 44 together define generally U-shaped flex portions 50a, 50b, respectively, for each of the fixation members 30a, 30b.

Each of the U-shaped flex portions 50a, 50b has a longitudinal dimension or depth, generally horizontally aligned in FIG. 2, that is larger than the diameter of the optic 20. In other words, the horizontal distance between the proximal end 36a, 36b and the U-bend 42a, 42b in each fixation member 30a, 30b is longer than the diameter of the optic 20. Indeed, in the relaxed state of the IOL 22, the inside leg 40a, 40b of each of the fixation members generally circumscribes the optic 20, covering an arc of approximately 135 degrees. The outside leg 44a, 44b of each of the fixation members is also arcuate, albeit in the opposite direction, but generally traverses a horizontal line.

When implanted, the fixation members 30a, 30b compress inward a slight amount, though not so much that the arespective elongate sections thereof touch each other or the optic. Because of the elongated nature of each of the fixation members 30a, 30b, and because of their indirect connection to the optic 20 via the cantilevered arm 38 and flange 26, relatively little of the compressive forces imparted by the eye are transferred to the optic. This reduces bowing or axial displacement of the optic. Further advantages of the configuration of the fixation members 30a, 30b will be described below with respect to FIG. 5.

Furthermore, due to the length of each of the flex portions 50a, 50b, a pair of outwardly directed footplates or pods 52, 54 is spaced apart a relatively long distance in comparison to IOLs of the prior art. In particular, the pods 52, 54 are spaced greater than 6 mm apart, and preferably between 7 and 9 mm apart. There are thus four pods 52, 54 in the exemplary embodiment generally evenly circumferentially spaced around the optical axis OA. This increased spacing and positioning provides increased stability to the intraocular lens 22, lowers the forces imparted to the optic 20 via the fixation members 30a, 30b which can be designed to decrease optic displacement along the optical axis OA, facilitates symmetric placement of a PC lens in the capsular bag, and potentially reduces the severity and occurrence of pupil ovalization.

In addition, the four pods 52, 54 are arranged on the flex portions 50a, 50b so that upon inward compression of between about 0.5–1.5 mm, the pods form a square in the iridio-corneal angle so as to reduce the chance of pupil ovalization. Desirably, each pod flexes inward about 1 mm, and the shape of the the fixation members 30a, 30b is such that the initially rectangular pod distribution as shown (in the relaxed, unimplanted state of the IOL) converts to a square. It should be noted that the relative movement of the two flex portions 50a, 50b is greater than the relative movement of the two pods 52, 54 on either flex portion, given their connection along the respective outside legs 44a, 44b. Therefore, the rectangular distribution of the pods 52, 54 (elongated along the 6/12 o'clock axis) converts to a square distribution upon implantation.

Each outside leg 44a, 44b spans from a first pod 52a, 52b adjacent the U-bend 42a, 42b to a second pod 54a, 54b at the distal end 46a, 46b of the respective fixation member 30a, 30b. Each pod 52, 54 is formed by an enlarged cross-section (in plan view) relative to the rest of the fixation member 30 and has an outer face (not numbered) with rounded corners that is angled so as to provide maximum comfort and stability to the patient. The outer faces are desirably angled so as to be generally concentric about the optical axis OA. That is, if the intraocular lens 22 is implanted in the anterior chamber, the outer faces of the pods 52, 54 present relatively large cross-sectional surfaces that contact the iridio-corneal angle. If the lens 22 is implanted in the posterior chamber, the outer faces of the pods 52, 54 provide large and symmetric surface area contact with the interior of the capsular bag. Because of their relatively great spacing and preferred outer face orientation, the combined four pods 52, 54 reduce irritation to the soft tissue of the iridio-corneal angle or the capsular bag.

Figure 2A:
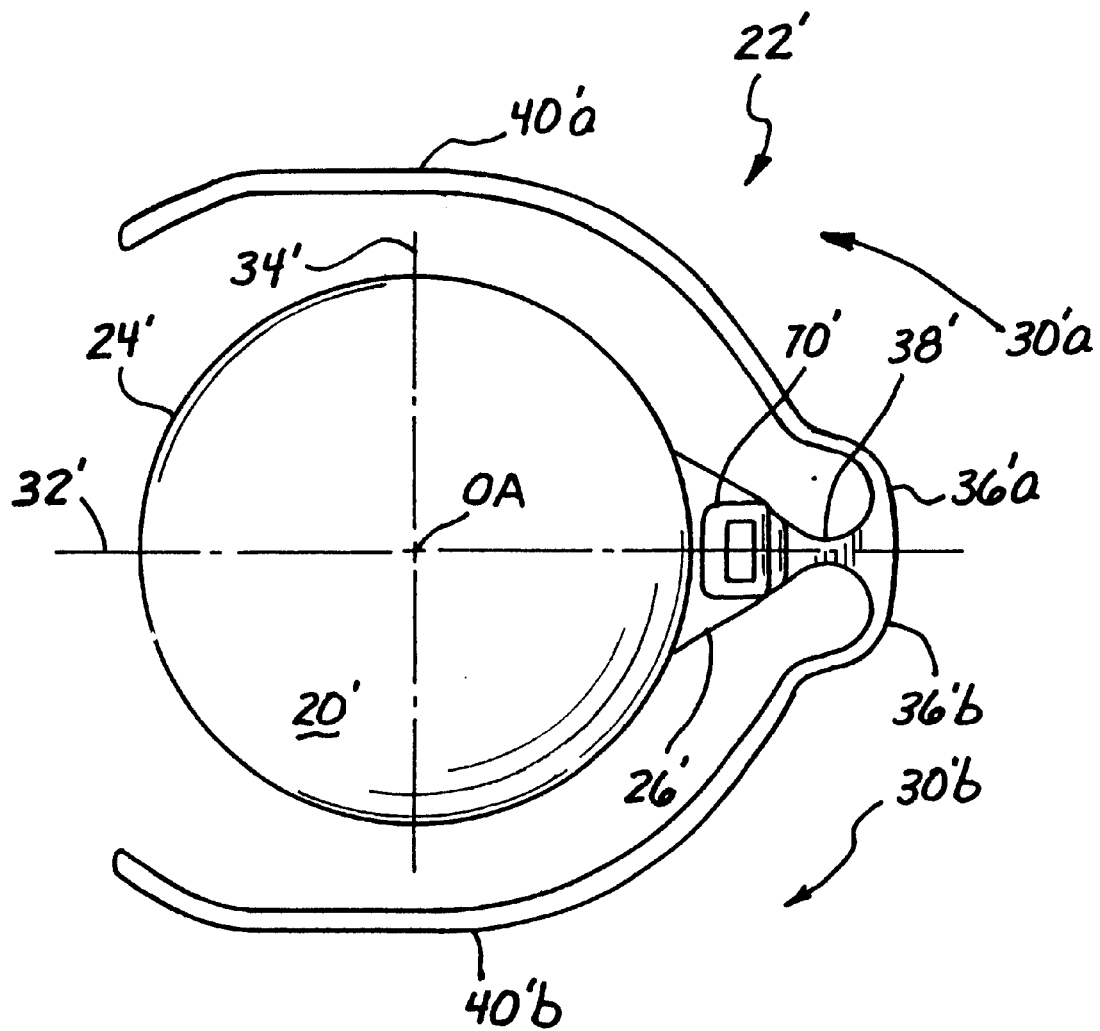
FIG. 2A is a plan view of an alternative intraocular lens of the present invention.

An alternative intraocular lens 22' seen in FIG. 2A in its relaxed, uncompressed state, includes an optic 20' and a pair fixation members 30a', 30b' adapted to support the optic in the center of the eye (whether placed in the anterior chamber, or in the capsular bag in the posterior chamber). Again, for purpose of orientation, perpendicular axes 32', 34' along the horizontal and vertical planes, respectively, are shown. The intraocular lens 22' is in many ways similar to the lens 22 of FIG. 2, and like parts will be denoted with the same numbers with the addition of a prime (').

As the earlier embodiment, the fixation members 30a', 30b' are desirably formed in a single piece connected at their proximal ends 36a', 36b' to a flange 26' via a cantilevered arm 38'. In an exemplary embodiment, the fixation members 30a', 30b' and cantilevered arm 38' are integrally formed such as by molding from a homogeneous material that is more rigid than that of the optic 20, although still somewhat flexible to enable folding during implantation (described below). Preferred materials are poly methyl methacrylate (PMMA) or polyether sulfone, although other similar materials may be used. It should be understood that any aspects of the invention described herein with respect to the earlier IOL 22 shown in FIG. 2 may apply to the alternative IOL 22' in FIG. 2A.

The flange 26' extends along the three o'clock direction, and thus both of the fixation members 30a', 30b' initially extend generally vertically in opposite directions from the outermost end of the cantilevered arm 38'. From their proximal ends 36a', 36b', the fixation members 30a', 30b', have elongated curvilinear legs 40a', 40b' defining flex portions of the IOL 22'. In contrast to the earlier embodiment, there is no outside leg, and no U-shaped flex portions.

The curvilinear legs 40a', 40b' have lengths that are greater than 6 mm, and preferably between 7 and 9 mm. This length provides increased stability to the intraocular lens 22', lowers the forces imparted to the optic 20' via the fixation members 30a', 30b' which can be designed to decrease optic displacement along the optical axis OA, facilitates symmetric placement of a PC lens in the capsular bag, and potentially reduces the severity and occurrence of pupil ovalization.

As mentioned above, the means of attaching the fixation members 30a, 30b to the optic 20 reduces the transmission of external forces on the fixation members to the optic. Indeed, the nature of the attachment is such that the fixation members are substantially decoupled from the optic. As seen in FIG. 2, the proximal ends 36a, 36b of the fixation members 30a, 30b come together at the outermost end of the cantilevered arm 38. The cantilevered arm 38, in turn, extends radially inward toward the optic 20 and attaches to the flange 26, as best seen in FIG. 3. It should be noted that the flange 26 illustrated in FIG. 3 is substantially rectangular in plan view, in contrast to the trapezoidal shape of the flange shown in FIGS. 1 and 2, although the structure and function is essentially the same.

As seen in FIG. 3, the cantilevered arm 38 has a main portion 60 that has a similar dimension in the plan view as in the axial direction, a paddle 62 that is relatively thin in the axial direction and wide in plan view, and a transition region 64 therebetween. The paddle 62 contacts one face of the flange 26 across a relatively large proportion of the surface area of the paddle. Indeed, as illustrated in FIG. 3, the rectangular flange 26 and paddle 62 have substantially the same width in the circumferential direction of the optic 20. The entire length of the cantilevered arm 38 including the main portion 60, transition region 64 and paddle 62 is desirably less than about 2 mm.

An attachment assembly seen in FIG. 3 includes the aforementioned flange 26, the paddle 62 of the cantilevered arm 38, and a coupling member 70. These three elements bond together using conventional means such as heat staking, laser welding, or ultrasonic welding. The coupling member 70 includes a relatively thin (in the axial dimension) and wide (in plan view) cover 72 that contacts the opposite side of the flange 26 from the paddle 62. In addition, the coupling member 70 includes an elongate step 74 projecting axially from the cover 72 that contacts the paddle 62.

The coupling member 70 is desirably made of the same material as the cantilevered arm 38, or at least of a material that easily and securely bonds thereto upon heat staking, laser welding, or ultrasonic welding. When these three elements are heated, laser welded, or ultrasonically welded, they join together to form a composite structure that is relatively strong and can withstand the forces associated with manipulation during implantation and the forces associated with normal use after implantation. Contact between the coupling member 70 and cantilevered arm 38 by virtue of the step 74 ensures direct bonding between these two elements, and effectively locks the flange 26 that is sandwiched therebetween in place.

FIG. 4 illustrates the underside of the coupling member 70 that is juxtaposed against the flange 26 and cantilevered arm 38. With reference back to FIG. 1, the flange 26 preferably includes an aperture 28. A similarly shaped projection 76 is provided on the underside of coupling member 70. Although not shown, the projection 76 fits closely within the aperture 28 and extends the same axial distance as the step 74 so as to contact the paddle 62. After heat staking, laser welding, or ultrasonic welding, this additional direct contact between the coupling member 70 and cantilevered arm 38, which are made of the same or very similar materials, further ensures a secure bond for the attachment assembly. Moreover, the projection 76 extends directly through the flange 26, and provides a positive anchor thereto. An enlarged window 78 seen in the middle of coupling member 70 may be useful in the mold process of forming the coupling member 70, but also serves the purpose of providing a cavity into which the material of the flange 26 may expand during the process of heat staking or ultrasonic welding.

It should be understood by those of skill in the art that various configurations of the attachment assembly in keeping with the principles of the present invention are envisioned. Indeed, the cantilevered arm 38 may include a forked end that fits around the flange 26, rather than providing a separate coupling member 70. Likewise, the coupling member 70 may be in the form of a sleeve that fits entirely around the juxtaposed flange 26 and cantilevered arm 38. Any of the configurations in accordance with the present invention enables attachment of relatively rigid fixation members to an ultrathin optic 20.

FIG. 3 illustrates the optic periphery 24 (for a meniscus type lens) that has a thickness of around 0.4 mm. The flange 26 has an even smaller thickness, and the sandwiched attachment assembly has about the same thickness as the optic 20. As seen by the transition region 64, the main portion 60 of the cantilevered arm 38 is somewhat thicker than the flange 26, as is the remainder of the fixation members 30a, 30b, though still not as thick as the optic periphery 24. Desirably, the fixation members 30a, 30b have a thickness in the axial dimension of about 0.25 mm.

As mentioned previously, the intraocular lens 22 of the present invention is particular well suited for minimally-invasive implant techniques through extremely small incisions, typically less than 5 mm, even as low as 3 mm. To enable this desirable insertion method, the fixation members 30a, 30b flex inward as seen by the arrow 80 in FIG. 5 on either side of the optic 20 to present an insertion profile having a dimension A. The dimension A is desirably less than 5 mm, and preferably about 3 mm. The fixation members 30a, 30b are flexed inward toward the 3/9 o'clock axis (see FIG. 2) using forceps, or other tools such as a Bartell-style injector.

Because the fixation members 30a, 30b are relatively rigid in comparison to the optic 20, they are the elements that must be reduced in profile to less than the size of the incision. The optic 20, on the other hand, is highly pliable and ultrathin and thus may be left unfolded during the insertion process. When the optic 20 passes through the incision, it naturally deforms and/or folds through the incision without damage to the adjacent tissue. In other words, the optic 20 is so thin and flexible that it deforms through the incision without manipulation, and then springs outward into its original disk shape in the anterior chamber or capsular bag. As a result, the method includes flexing both of the fixation members 30a, 30b toward one another so that they overlap within the diameter of the optic 20 and define a profile of less than about 5 mm, and passing the intraocular lens 22 in the direction of the 3/9 o'clock axis through an incision of 5 mm or less without otherwise manipulating the optic into a fold.

While this invention has been described with respect to various specific examples and embodiments, it is to be understood that the invention is not limited thereto and that it can be variously practiced within the scope of the following claims.

What is claimed is:

1. A foldable intraocular lens for implantation in the eye, the intraocular lens comprising:

an optic centered on an optical axis and made of a highly pliable material, the optic having a generally circular periphery and an integral flange extending radially outward therefrom;

a cantilevered arm made of a material that is flexible but more rigid than the material of the optic, the arm being attached to the optic, the arm extending radially outward from the periphery of the optic and including a paddle that overlaps one side of the flange, a main elongate portion, and an outer end;

a pair of fixation members integral with the cantilevered arm for supporting the optic centered on the optical axis of the eye, each fixation member having a proximal end at the outer end of the cantilevered arm, a distal end, and a flex portion intermediate the proximal and distal ends, wherein the flex portions extend generally away from one another adjacent to their respective proximal ends on diametrically-opposed sides of the optic; and a coupling member separate from the optic and cantilevered arm, the coupling member including a portion that overlaps the flange on the side opposite the paddle, and a stepped edge that has approximately the same thickness as the flange, the coupling member and paddle sandwiching the flange therebetween and the stepped edge of the coupling member directly contacting the cantilevered arm, wherein the cantilevered arm flange, and coupling member define an attachment assembly, the assembly being bonded together.

2. The intraocular lens of claim 1, wherein the material of the optic is selected from the group consisting of:

silicone;

hydrophilic acrylic; and hydrophobic acrylic.

3. The intraocular lens of claim 2, wherein the material of the cantilevered arm and fixation members is selected from the group consisting of:

PMMA; and polyether sulfone.

4. The intraocular lens of claim 1, wherein the optic is a meniscus type of optic and has a center thickness of less than about 0.5 mm.

5. The intraocular lens of claim 1, wherein the fixation members have a thickness and flexibility that enable them to be folded inward toward one another so as to overlap the optic and present a smaller insertion profile than the diameter of the optic.

6. The intraocular lens of claim 1, wherein the assembly is bonded together using a method selected from the group consisting of:

heat staking;

laser welding; and ultrasonic welding.

7. The intraocular lens of claim 1, wherein the cantilevered arm and flange are attached together using a method selected from the group consisting of:

heat staking;

laser welding; and ultrasonic welding.

8. The intraocular lens of claim 1, wherein the flex portions of the fixation members extend generally away from one another adjacent to their respective proximal ends and then turn twice to form substantial U-shapes that have lengths greater than the diameter of the optic, the U-shapes being oriented generally in parallel on diametrically-opposed sides of the optic.

9. The intraocular lens of claim 8, wherein the lens is adapted for anterior chamber implantation and each flex portion of each fixation member includes a pair of spaced apart pods for contacting the iridio-corneal angle in the anterior chamber.

10. The intraocular lens of claim 9, wherein each pair of pods is spaced apart at least seven mm.

11. The intraocular lens of claim 1, wherein the lens is adapted for anterior chamber implantation and each flex portion of each fixation member includes a pair of spaced apart pods for contacting the iridio-corneal angle in the anterior chamber, wherein the four pods are arranged on the flex portions so that upon inward compression of between about 0.5–1.5 mm, they form a square in the iridio-corneal angle so as to reduce the chance of pupil ovalization.

12. A foldable intraocular lens for implantation in the eye, the intraocular lens comprising:
    an optic centered on an optical axis and made of a highly pliable material, the optic having a generally circular periphery and an integral flange extending radially outward therefrom;
    a cantilevered arm made of a material that is flexible but more rigid than the material of the optic, the arm extending radially outward from the optic periphery and including a paddle overlapping one end of the flange, a main elongate portion, and an outer end;
    a pair of fixation members integral with the cantilevered arm for supporting the optic centered on the optical axis of the eye, each fixation member having a proximal end at the outer end of the cantilevered arm, a distal end, and a flex portion intermediate the proximal and distal ends, the flex portions being oriented generally in parallel on diametrically-opposed sides of the optic; and
    a coupling member separate from the optic and cantilevered arm, the coupling member including a portion that overlaps the flange on the side opposite the paddle and a stepped edge that has approximately the same thickness as the flange, the coupling member and paddle sandwiching the flange therebetween and the stepped edge of the coupling member directly contacting the cantilevered arm, wherein the cantilevered arm, flange, and coupling member define an attachment assembly, the assembly being bonded together using a method selected from the group consisting of:
        heat staking;
        laser welding; and
        ultrasonic welding.

13. The intraocular lens of claim 12, wherein the fixation members have a thickness and flexibility that enable them to be folded inward toward one another so as to overlap the optic and present a smaller insertion profile than the diameter of the optic.

14. The intraocular lens of claim 12, wherein the flex portions of the fixation members extend generally away from one another adjacent to their respective proximal ends and then turn twice to form substantial U-shapes that have lengths greater than the diameter of the optic, the U-shapes being oriented generally in parallel on diametrically-opposed sides of the optic.

15. The intraocular lens of claim 14, wherein the lens is adapted for anterior chamber implantation and each flex portion of each fixation member includes a pair of spaced apart pods for contacting the iridio-corneal angle in the anterior chamber.

16. The intraocular lens of claim 15, wherein each pair of pods is spaced apart at least seven mm.

17. The intraocular lens of claim 12, wherein the lens is adapted for anterior chamber implantation and each flex portion of each fixation member includes a pair of spaced apart pods for contacting the iridio-corneal angle in the anterior chamber, wherein the four pods are arranged on the flex portions so that upon inward compression of between about 0.5–1.5 mm, they form a square in the iridio-corneal angle so as to reduce the chance of pupil ovalization.

18. A foldable intraocular lens for implantation in the eye, the intraocular lens comprising:
    an optic centered on an optical axis and made of a highly pliable material, the optic having a generally circular periphery and an integral flange extending radially outward therefrom;
    at least one fixation member for supporting the optic centered on the optical axis of the eye, the at least one fixation member having a proximal end, a distal end, and a flex portion intermediate the proximal and distal ends, the proximal end having an arm extending toward the optic and a paddle on an end thereof that overlaps the flange and is connected thereto; and
    a coupling member separate from the optic and fixation member and including a portion that overlaps the flange, and a stepped edge that has approximately the same thickness as the flange, the coupling member and paddle sandwiching the flange therebetween and the stepped edge of the coupling member directly contacting the arm, wherein the arm, flange, and coupling member define an attachment assembly, the assembly being bonded together.

19. The intraocular lens of claim 18, wherein the material of the optic is selected from the group consisting of:
    silicone;
    hydrophilic acrylic; and
    hydrophobic acrylic.

20. The intraocular lens of claim 19, wherein the at least one fixation member, arm and paddle are integrally formed of a material that is flexible but more rigid than the material of the optic.

21. The intraocular lens of claim 20, wherein the material of the arm and the at least one fixation member is selected from the group consisting of:
    PMMA; and
    polyether sulfone.

22. The intraocular lens of claim 18, wherein the optic is a meniscus type of optic and has a center thickness of less than about 0.5 mm.

23. The intraocular lens of claim 18, wherein the at least one fixation member comprises a pair of fixation members integral with the arm for supporting the optic centered on the optical axis of the eye, and wherein the flex portions are oriented generally in parallel on diametrically-opposed sides of the optic.

24. The intraocular lens of claim 23, wherein the flex portions of the fixation members extend generally away from one another adjacent to their respective proximal ends and then turn twice to form substantial U-shapes that have lengths greater than the diameter of the optic, the U-shapes being oriented generally in parallel on diametrically-opposed sides of the optic.

25. The intraocular lens of claim 18, wherein the attachment assembly is bonded together using a method selected from the group consisting of:

heat staking;

laser welding; and ultrasonic welding.

26. The intraocular lens of claim 18, wherein the flange includes an aperture and the coupling member has a projection that fits through the aperture and contacts the paddle on the other side of the flange.

27. The intraocular lens of claim 18, wherein the arm, paddle, and coupling member of the at least one fixation member are made of the same material, and the attachment assembly is bonded together using heat such that the portions in direct contact fuse together.

* * * * *